United States Patent [19]

Nejib et al.

[11] Patent Number: 4,950,015
[45] Date of Patent: Aug. 21, 1990

[54] SYRINGE CAP CLAMP TOOL

[75] Inventors: Umid R. Nejib, Trucksville; James J. Lennox, Berwick; George M. Sarnecky, White Haven; Larry C. Sickler, Falls, all of Pa.

[73] Assignee: Design Specialties Laboratories, Inc., Kingston, Pa.

[21] Appl. No.: 300,124

[22] Filed: Jan. 23, 1989

[51] Int. Cl.⁵ .................... A61M 5/32; B25B 13/52; B25J 15/00
[52] U.S. Cl. ................... 294/19.1; 81/3.43; 81/64; 128/919; 294/31.2; 294/100
[58] Field of Search .......... 294/19.1, 19.3, 22, 294/26, 31.2, 50.8, 50.9, 99.1–100, 103.1, 115, 116; 81/64, 65, 3.43; 119/151, 153, 154; 128/303 R, 325, 346, 354, 917, 919; 604/192, 198, 263; 606/151, 157, 205

[56] References Cited

U.S. PATENT DOCUMENTS

| | | | |
|---|---|---|---|
| 437,647 | 9/1890 | Franklin | 294/99.2 |
| 1,343,213 | 6/1920 | Johnson et al. | 119/153 |
| 1,463,776 | 7/1923 | Knudtson | 119/153 |
| 1,724,435 | 8/1929 | Studwell | 294/19.1 |
| 2,191,170 | 2/1940 | Keehn et al. | 294/19.3 |
| 2,320,967 | 6/1943 | Dunkelberger | 294/100 |
| 2,723,152 | 11/1955 | Doty | 294/19.3 X |
| 3,043,308 | 7/1962 | Seltzer | 128/346 |
| 3,507,270 | 4/1970 | Ferrier | 128/346 X |
| 3,540,769 | 11/1970 | Rosser | 294/19.1 |
| 3,949,514 | 4/1976 | Ramsey | 119/153 X |
| 4,106,508 | 8/1978 | Berlin | 128/346 |
| 4,532,833 | 8/1985 | Downs | 294/31.2 |

FOREIGN PATENT DOCUMENTS 2205043  11/1988  United Kingdom ............ 604/198

Primary Examiner—Johnny D. Cherry
Attorney, Agent, or Firm—Nies, Kurz, Bergert & Tamburro

[57] ABSTRACT

A tool for gripping and manipulating an article, the tool being particularly useful in removing and replacing a cap on a needle of a hypodermic syringe. The tool is held and manipulable in one hand and includes a clamp element, an actuator movable between locked and release positions and a lock mechanism for locking the actuator in its locked position. The lock mechanism is easily depressed by the thumb to release the actuator and close the clamp element on the cap.

8 Claims, 3 Drawing Sheets

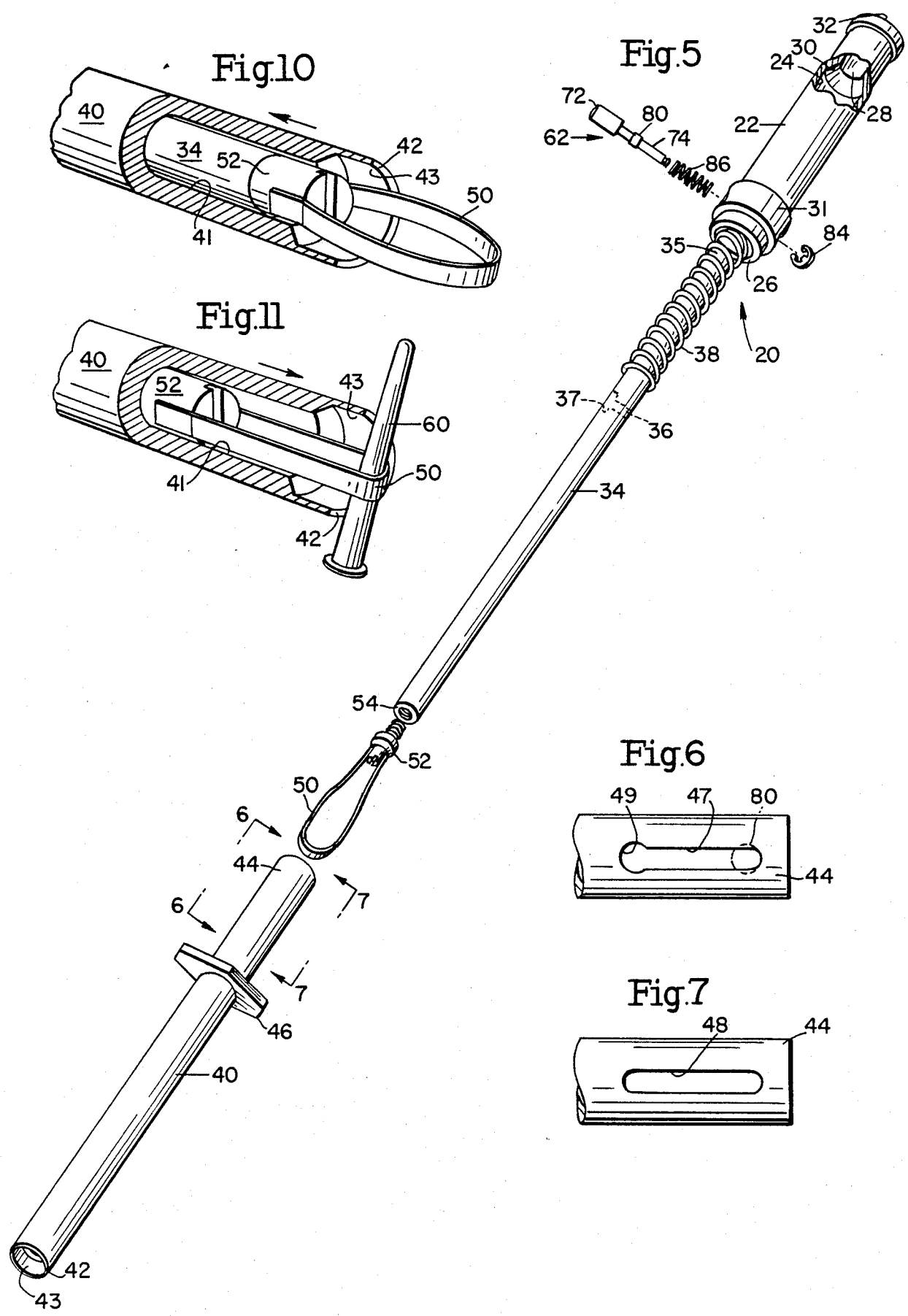

SYRINGE CAP CLAMP TOOL

BACKGROUND OF THE INVENTION

This invention relates generally to a clamp or pick up tool for holding or manipulating articles, and more particularly to a novel tool useful in the medical field.

Medical personnel are increasingly exposed to blood diseases such as AIDS. A primary source of those diseases is a used, bloodied needle, e.g. on a hypodermic syringe, by which the personnel may be accidentally scratched or pricked. It is desirable to recap a used needle, but this commonly requires a medical person to place his hands close to the needle, thereby increasing chances of an accident.

SUMMARY OF THE INVENTION

Accordingly, a primary object of this invention is to provide a novel, compact, reliable, safe clamp tool which is manipulable with one hand.

A further object of the invention is to provide the above novel tool particularly useful for removing and then replacing a cap on a used needle of a medical device such as a hypodermic syringe, the tool enabling a medical person to keep his hand away from the needle.

Another object is to provide the above novel tool which has a clamp element, an actuator movable between a locked position and a release position, and a latch mechanism holding the actuator in its locked position but releasable to free the actuator to close the clamp element on the cap.

Still another object is to provide the above novel tool wherein the clamp element is a flexible, epansible loop which accommodates and holds firmly articles of various sizes and shapes.

Other objects and advantages will become apparent as the description proceeds in connection with the accompanying drawings.

BRIEF DESCRIPTION OF THE DRAWINGS

FIG. 5 is a perspective view similar to FIG. 1, but with the parts illustrated in exploded form;

FIG. 6 is a fragmentary view taken along line 6—6 of FIG. 5;

FIG. 7 is fragmentary view taken along line 7—7 of FIG. 5;

FIG. 10 is a fragmentary sectional view of the tool with the parts in the locked position, the clamp loop being exposed and open, ready to grasp an article; and FIG. 11 is a view similar to FIG. 10 but with the parts in the unlocked position, the clamp loop firmly grasping an article.

DETAILED DESCRIPTION OF THE INVENTION

Figure 1:
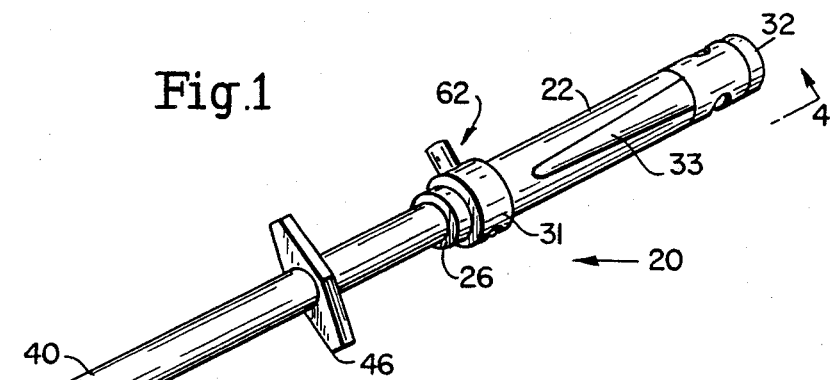
FIG. 1 is a general perspective view of the novel tool of the invention with the parts in the unlocked condition.

Referring now to the drawings, the novel clamp and pick-up tool 20 of the invention, shown about actual size in FIGS. 1–4, is small, compact, lightweight, and conveniently manipulable with one hand.

Tool 20 comprises base 22 having a cylindrical bore 24 extending inwardly from one end 26 and terminating at shoulder 28 and counterbore 30. An enlarged collar 31 is formed adjacent open end 26. The other end 32 is closed. A pocket clip 33 may be provided for convenience.

An elongated circular guide rod 34, of a diameter smaller than that of bore 24, has its inner end 35 fixed, e.g. by a press fit, within counterbore 30. A drilled hole 36 with a counterbore 37 extends tranversely through rod 34. Coil spring 38 surrounds rod 34 within bore 24.

Figure 8:
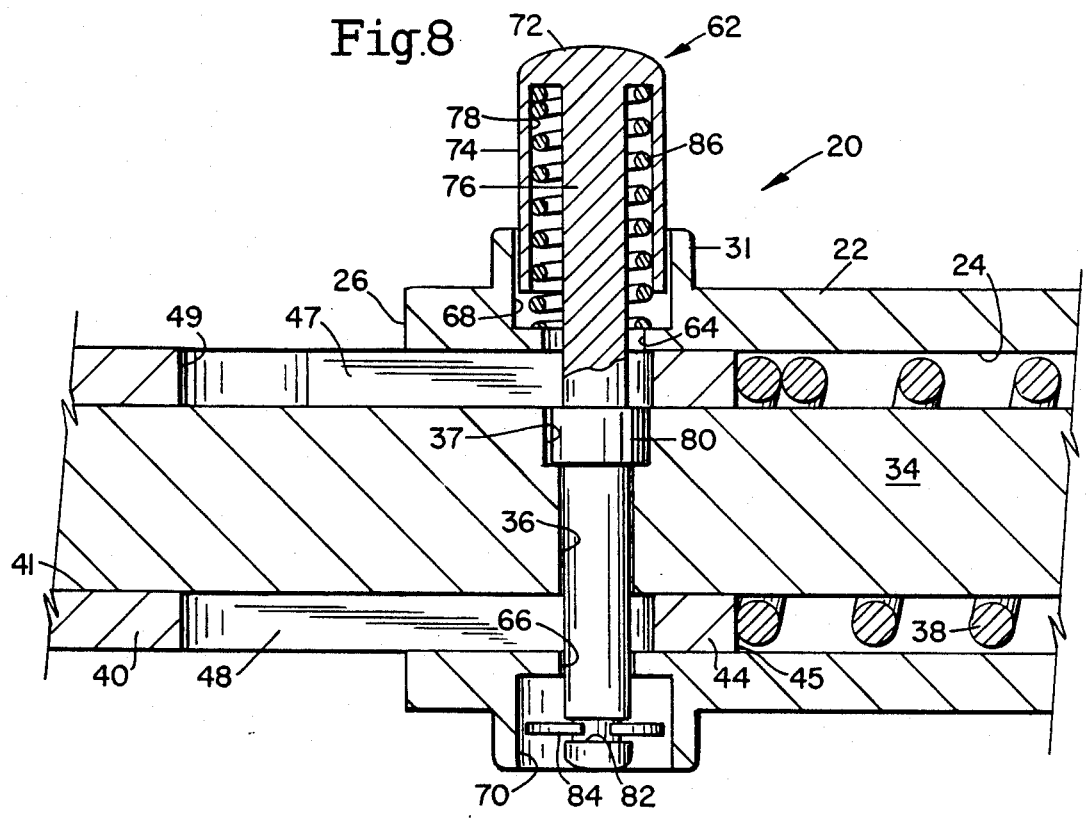
FIG. 8 is a fragmentary sectional view taken along line 8—8 of FIG. 4 and illustrating the parts in their unlocked position.
Figure 9:
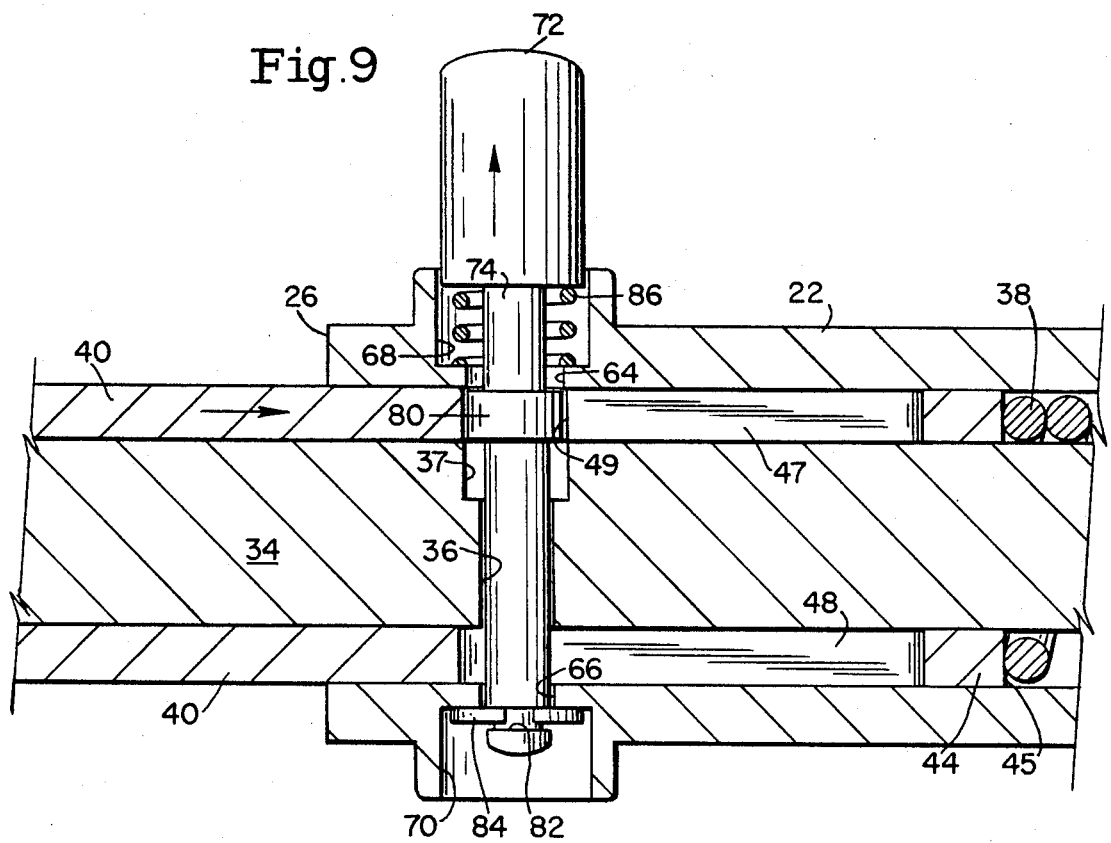
FIG. 9 is a fragmentary sectional view taken along line 9—9 of FIG. 4, but illustrating the parts in their locked position.

An outer tubular actuating sleeve 40 has an internal bore 41 by which it slides over rod 34, and outer end face 42, and an enlarged end counterbore 43. Inner end 44 of sleeve 40 slides within bore 24 and its end face 45 is biased against spring 38. (FIGS. 8 and 9). A finger grip element 46 is fixed on the outside of sleeve 40. As shown in FIGS. 6 and 7, longitudinally extending slots 47 and 48 are on opposite sides of sleeve 40 adjacent end 44, with slot 47 having an enlarged opening 49 at its outer end.

A clamp element in the form of a thin expansible endless loop 50, e.g. a metal spring loop, is welded onto a screw 52 which thread into the outer end 54 of rod 34.

Figure 2:
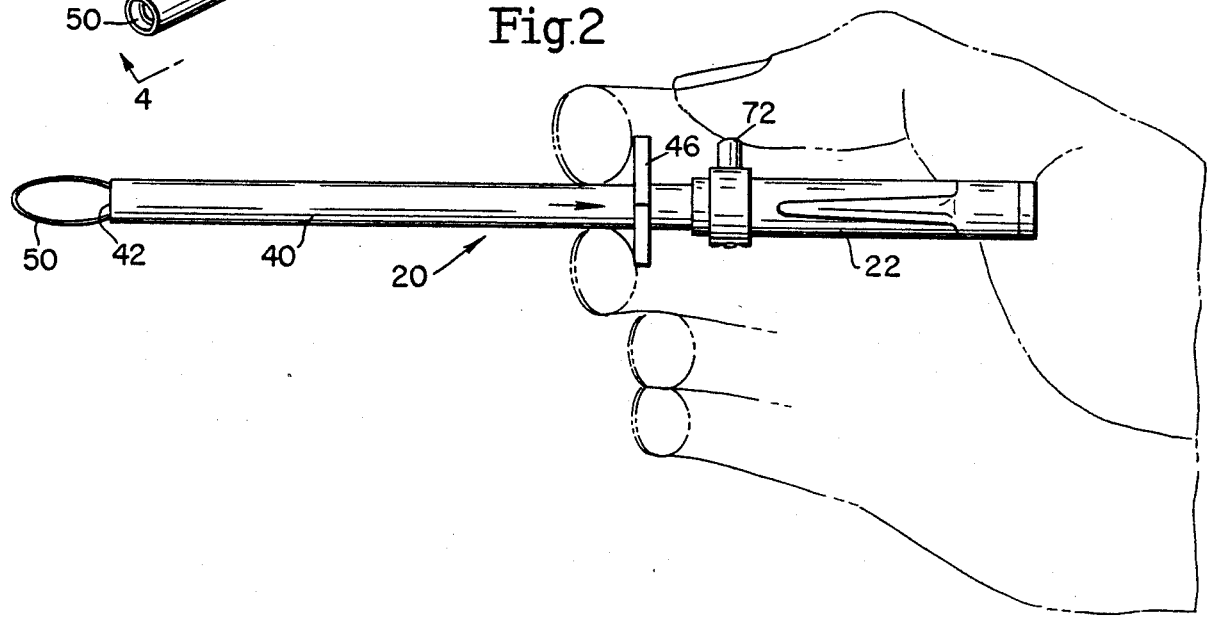
FIG. 2 is a view of the tool illustrating the parts in the locked position and the clamp loop exposed and open, ready to grasp an article.
Figure 4:
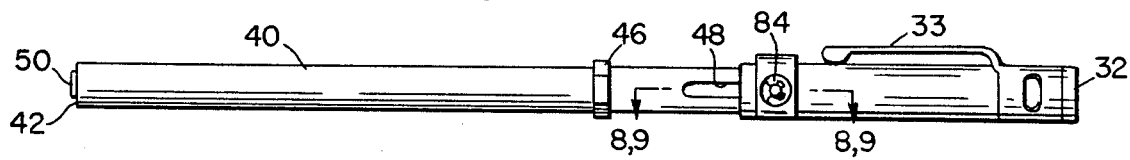
FIG. 4 is a side elevation view taken along line 4—4 of FIG. 1.

Sleeve 40 reciprocates in and out on rod 34 against the bias of spring 38 between a locked, retracted position shown in FIGS. 2 and 9 and 10 and and unlocked, or release position of FIGS. 1, 4 and 8.

A releasable lock mechanism 62, shown best in FIGS. 8 and 9, includes aligned openings 64 and 66 drilled through collar 31, the openings aligning with opening 36 and counterbore 37 of rod 34 when the rod is fixed in place. Openings 64 and 66 have outer counterbores 68 and 70, respectively. A latch pin 72 consists of a head 74 and a shaft 76 extending from the base of the head and defining an annular space 78 therewith. The diameter of shaft 76 is less than the width of slots 47 and 48, so that the shaft passes therethrough, permitting reciprocation of sleeve 40 but prohibiting rotation thereof. Shaft 76 has an intermediate ring section 80 of somewhat enlarged diameter and a groove 82 adjacent its distal end for receiving a snap ring 84. A compressed coil spring 86 fits over ring section 80 around shaft 76 within annular space 78.

The diameter of ring section 80 is smaller than the diameter of openings 64 and 49, but larger than the width of slot 47 as shown in phantom in FIG. 6. Thus ring 80 can enter opening 49, but not slot 47.

To assemble the components, sleeve 40 is pushed inwardly on rod 34, compressing spring 38, to the locked position of FIG. 9 wherein openings 64, 49, 36 and 66 and slot 48 are in alignment. With spring 86 nested within space 78, shaft 76 is inserted through the aligned openings until ring 80 rests within counterbore 37 (as in FIG. 8), whereupon snap ring 84 is installed in groove 82 to hold latch pin 72 in place.

When tool 20 is not in use, sleeve 40 is normally in its unlocked or release position shown in FIGS. 1 and 4.

The sleeve is extended outwardly on rod 34 with loop 50 being enclosed and collapsed within bore 41 and counterbore 43 (FIG. 11). Latch pin 72 is depressed so that spring 86 is compressed and ring 80 rests in counterbore 37 (FIG. 8) bearing against the bottom of slot 47 (FIG. 6).

When it is desired to use tool 20, e.g. to remove a needle cap 60 from a hypodermic syringe held in the left hand by a medical person, the tool is held in the person's right hand (FIG. 2) with base 22 nested in the palm of the hand and sleeve 40 and grip 46 secured by two fingers. Sleeve 40 is pulled inwardly until opening 49 aligns with ring 80 which then snaps upwardly into opening 49 as shown in FIG. 9. Sleeve 40 is thus locked in its retracted position, spring 38 is compressed, and loop 50 is in its exposed, open, expanded position extending beyond end face 42. Loop 50 is then slipped over cap 60, latch pin 72 is depressed by the thumb to move ring 80 out of opening 49 down into counterbore 37, thereby releasing sleeve 40 which is rapidly pushed outwardly by spring 38 to close loop 50. Cap 60 is thus squeezed tightly by loop 50 against end face 42 (FIGS. 3 and 11), and is easily removed to expose the needle.

Figure 3:
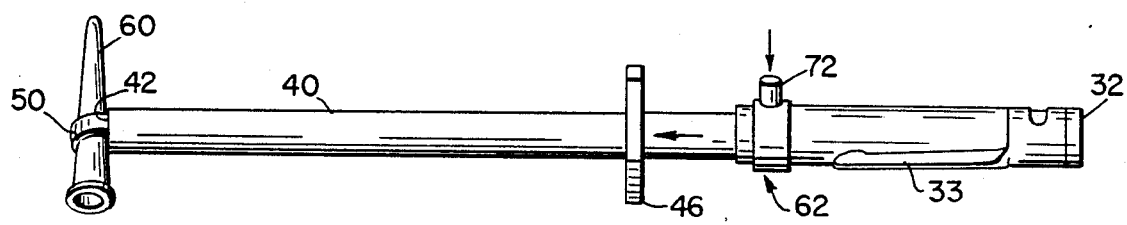
FIG. 3 is a view similar to FIG. 2, but with the parts unlocked and the loop firmly holding an article, such as a needle cap from a hypodermic syringe.

After the injection has been given and the bloodied needle is removed from the patient, cap 60, still held by tool 20 as in FIG. 3, is quickly and firmly placed over the used needle. Once the cap is in place, finger grip 46 is again pulled to move sleeve 40 inwardly to the retracted locked position of FIGS. 2 and 9. Loop 50 thus expands and is easily removed off the end of cap 60.

At no time does the hand holding tool 20 get near the used needle. Thus, the danger of the medical person being pricked by the used needle is virtually eliminated.

From the description hereinabove, it is apparent that the invention advantageously provides a small, compact, lightweight reliable tool which is easily manipulable with one hand and which substantially reduces accidental pricks from used needles and the corresponding exposure to deadly diseases. The needle cap 60, or any other article, is firmly gripped within loop 50 against end face 42 under the bias of compressed spring 38.

Because loop 50 is flexible and expansible it can accommodate articles of different sizes and shapes. Also, because sleeve 40 is locked via mechanism 62 in it s retracted position while loop 50 is being placed over cap 60, the fingers holding sleeve 40 may be relaxed to facilitate manipulation of the tool by the person.

While tool 20 is particularly useful by medical personnel, it may also be used to handle other articles of various sizes and shapes.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A tool which can be held and manipulated eith one hand comprising base means, rod means having an inner end connected to said base means and an outer end extending longitudinally therefrom, sleeve means mounted on said rod means for longitudinal sliding movement between an inner locked position and an outer release position, article clamp means connected to the outer end of said rod means, said clamp means being open when said sleeve means is in said locked position and being closed on an article when said sleeve means is in said release position, spring means mounted within said base means for biasing said sleeve means from said locked position to said release position, locking means connected to said base means for locking said sleeve means in said locked position, finger grip means mounted on said sleeve means at a location closely adjacent said base means, whereby when using the tool said base means rests within the palm of the hand, said finger grip means is engageable by the fingers of the same hand to move said sleeve means from said release position to said locked position, and said locking means is quickly releasable to free said sleeve means to said release position.

2. A tool according to claim 1, said clamp means being an expansible endless loop.

3. A tool according to claim 1, said locking means comprising a latch pin extending tranversely through said base means, said sleeve means, and said rod means, said pin being movable between an outer latching position in which it holds said sleeve means in said locked position and an inner unlatching position in which frees said sleeve means for movement to its release position, and latching spring means biasing said latch pin from said unlatching position to said latching position.

4. A tool according to claim 3, said sleeve means including longitudinal slot means through which said pin extends, said slot means having an enlarged opening at one end, said pin having a ring section of a diameter smaller than said opening but larger than said slot means, whereby when said opening aligns with said ring section said pin moves to its outer latching position to hold said sleeve means in its locked position.

5. A took which can be held and manipulated with one hand comprising base means, rod means having an inner end connected to said base means and an outer end extending longitudinally therefrom, sleeve means mounted on said rod means for longitudinal sliding movement between an inner locked position and an outer release position, article clamp means connected to the outer end of said rod means, said clamp means being open when said sleeve means is in said locked position and being closed on an article when said sleeve means is in said release position, spring means mounted against said base means for biasing said sleeve means from said locked position to said release position, said sleeve means including longitudinal slot means having an enlarged opening at one end, locking means for locking said sleeve means in said locked position, said locking means being quickly releasable to free said sleeve means to said release position, said locking means comprising a latch pin extending transversely through said base means, said slot means of said sleeve means, and said rod means, said pin being movable between an outer latching position in which it holds said sleeve means in said locked position and an inner unlatching position in which it frees said sleeve means for movement to its release position, said pin having a ring section of a diameter smaller than said opening but larger than said slot means, whereby when said opening aligns with said ring section, said pin moves to its outer latching position to hold said sleeve means in its locked position, and latching spring means biasing said latch pin from said unlatching position to said latching position.

6. A tool according to claim 5, said clamp means being an expansible endless loop.

7. A tool which can be held and manipulated with one hand comprising base means having a cylindrical bore, rod means having an inner end mounted within said bore and an outer end extending longitudinally therefrom, sleeve means having an inner end located within said bore, said sleeve means mounted on said rod means for longitudinal sliding movement between an inner locked position and an outer release position, article clamp means connected to the outer end of said rod means, said clamp means being open when said sleeve means is in said locked position and being closed on an article when said sleeve means is in said release position, spring means mounted within said bore for biasing said sleeve means from said locked position to said release position, locking means connected to said base means for locking said sleeve means in said locked position, said locking means including a latch pin extending transversely into said bore and into the inner end of said sleeve means, said pin being movable between an outer latching position in which it holds said sleeve means in said locked position and an inner unlatching position in which it frees said sleeve means for movement to release position, latching spring means biasing said latch pin from said unlatching position to said latching position, finger grip means mounted on said sleeve means at a location closely adjacent said base means, whereby when using the tool, said base means rests within the palm of the hand, said finger grip means is engageable by the fingers of the same hand to move said sleeve means from said release position to said locked position, and said latch pin is engageable by the same hand to quickly free said sleeve means for movement to said release position.

8. A tool according to claim 7, said clamp means comprising an expansible loop.

* * * * *